(12) United States Patent
Rodgers et al.

(10) Patent No.: US 7,122,523 B2
(45) Date of Patent: Oct. 17, 2006

(54) METHODS FOR INHIBITING TUMOR CELL PROLIFERATION

(75) Inventors: Kathleen E. Rodgers, Long Beach, CA (US); Gere S. diZerega, San Luis Obispo, CA (US)

(73) Assignee: University of Southern California, Los Angeles, CA (US)

( * ) Notice: Subject to any disclaimer, the term of this patent is extended or adjusted under 35 U.S.C. 154(b) by 413 days.

(21) Appl. No.: 10/133,517

(22) Filed: Apr. 26, 2002

(65) Prior Publication Data

US 2004/0176302 A1 Sep. 9, 2004

Related U.S. Application Data

(60) Provisional application No. 60/287,760, filed on May 1, 2001.

(51) Int. Cl.
*A61K 38/00* (2006.01)
*A61K 38/04* (2006.01)

(52) U.S. Cl. ............................. 514/16; 514/2; 530/329

(58) Field of Classification Search .................. 514/16, 514/17, 12; 530/316, 327, 328, 329; 930/40
See application file for complete search history.

(56) References Cited

U.S. PATENT DOCUMENTS

| | | | | |
|---|---|---|---|---|
| 3,750,653 | A | * | 8/1973 | Simon ........................... 600/6 |
| 4,937,254 | A | | 6/1990 | Sheffield et al. |
| 5,015,629 | A | * | 5/1991 | diZerega ..................... 514/16 |
| 5,629,292 | A | | 5/1997 | Rodgers et al. |
| 5,693,616 | A | | 12/1997 | Krstenansky et al. |
| 5,716,935 | A | | 2/1998 | Rodgers et al. |
| 5,834,432 | A | | 11/1998 | Rodgers et al. |
| 5,955,430 | A | | 9/1999 | Rodgers et al. |
| 5,977,159 | A | | 11/1999 | Fandriks et al. |
| 5,981,568 | A | | 11/1999 | Kunz et al. |
| 6,017,522 | A | * | 1/2000 | Butterfield et al. ....... 424/78.37 |
| 6,096,709 | A | | 8/2000 | Rodgers et al. |
| 6,110,895 | A | | 8/2000 | Rodgers et al. |
| 6,165,978 | A | | 12/2000 | Rodgers et al. |
| 6,177,407 | B1 | | 1/2001 | Rodgers et al. |
| 2003/0203834 | A1 | | 10/2003 | Tallant et al. |

FOREIGN PATENT DOCUMENTS

| | | | |
|---|---|---|---|
| WO | WO 9003768 | | 4/1990 |
| WO | WO 99/45945 | * | 9/1999 |

OTHER PUBLICATIONS

Bailar et al., Cancer Undefeated, New England Journal of Medicine, vol. 336, No. 22, pp. 1569-1574.*

Gura, T., Science, 1997, vol. 278, No. 5340, pp. 1041-1042.*

Bailar et al. (New England Journal of Medicine, 1997, vol. 336, No. 22, pp. 1569-1574.*

Bailar III, et al., (1997), N. Engl. J. Med., "Cancer Undefeated", vol. 336 (22), pp. 1569-1574.

Kunapuli, et al., (1987), Circulation Research, "Molecular cloning of human angiotensinogen CDNA and evidence for the presence of its mRNA in rat heart", vol. 60 (5), pp. 786-790.

Clouston, et al., (1988), Genomics, "Molecular cloning of the mouse angiotensinogen gene", vol. 2, pp. 240-248.

Kageyama, et al., (1984), Biochemistry, "Primary structure of human preangiotensinogen deduced from the cloned cDNA sequence", vol. 23, pp. 3603-3609.

Ohkubo, et al., (1983), Proc. Natl. Acad. Sci., Cloning and sequence analysis of cDNA for rat angiotensinogen, vol. 80, pp. 2196-2200.

Dzau, et al., (1989), J. Mol. Cell. Cardiol., "Molecular mechanism of angiotensin in the regulation of vascular and cardiac growth", vol. 21, pp. S7 (Supp III).

Berk, et al., (1989), Hypertension, "Angiotensin II-stimulated protein synthesis in cultured vascular smooth muscle cells", vol. 13 (4), pp. 305-314.

Kawahara, et al., (1988), BBRC, "Angiotensin II induces expression of the C-FOS gene through protein kinase C activation and calcium ion mobilization in cultured vascular smooth muscle cells", vol. 150 (1), pp. 52-59.

Naftilan, et al., (1989), J. Clin. Invest., "Induction of platelet-derived growth factor A-chain and c-*myc* gene expressions by angiotensin II in cultured rat vascular smooth muscle cells", vol. 83, pp. 1419-1424.

Taubman, et al., (1989), J. Biol. Chem., "Angiotensin II induces c-*fos* mRNA in aortic smooth muscle", vol. 264 (1), pp. 526-530.

Nakahara, et al., (1992), BBRC, "Identification of three types of PDGF-A chain gene transcripts in rabbit vascular smooth muscle and their regulated expression during development and by angiotensin II", vol. 184 (2), pp. 811-818.

Stouffer and Owens, (1992), Circ. Res., "Angiotensin II-induced mitogenesis of spontaneously hypertensive rat-derived cultured smooth muscle cells is dependent on autocrine production of transforming growth factor-$\beta$", vol. 70 (4), pp. 820-828.

(Continued)

*Primary Examiner*—B. Dell Chism
(74) *Attorney, Agent, or Firm*—McDonnell Boehnen Hulbert & Berghoff LLP

(57) ABSTRACT

The present invention provides methods, compounds, and pharmaceutical compositions for inhibiting tumor cell proliferation, by administering an effective amount of angiotensinogen, angiotensin I (AI), AI analogues, AI fragments and analogues thereof, angiotensin II (AII), AII analogues, AII fragments or analogues thereof or AII $AT_2$ type 2 receptor agonists to a subject.

5 Claims, No Drawings

OTHER PUBLICATIONS

Wolf, et al., (1992), Am. J. Pathol., "Angiotensin II stimulates the proliferation and biosynthesis of type I collagen in cultured murine mesangial cells", vol. 140 (1), pp. 95-107.

Bell and Madri, (1990), Am. J. Pathol., "Influence of the angiotensin sustem on endothelial and smooth muscle cell migration", vol. 137 (1), pp. 7-12.

Fernandez, et al., (1985), J. Lab. Clin. Med., "Neovascularization produced by angiotensin II", vol. 105(2), p. 141.

LeNoble, et al., (1991), Eur. J. Pharmacol., "Angiotensin II stimulates angiogenesis in the chorio-allantoic membrane of the chick embryo", vol. 195, pp. 305-306.

Shanugam, et al., (1995), Am. J. Physiol., "Expression of angiotensin II $AT_2$ receptor mRNA during development of rat kidney and adrenal gland", vol. 268, pp. F922-F930.

Helin, et al., (1997), Annals of Medicine, "The role of angiotensin receptors in cardiovascular diseases", vol. 29, pp. 23-29.

Bedecs, et al., (1997), Biochem J., "Angiotensing II type 2 receptors mediate inhibition of mitogen-activated protein kinase cascade and functional activation of SHP-1 tyrosine phosphatase", vol. 325, pp. 449-454.

Stecklings, et al., (1996), Biochem. Biophys. Res. Commun., "Angiotensin II stimulates proliferation of primary human keratinocytes via a Non-$AT_1$, Non-$AT_2$ angiotensin receptor", vol. 229, pp. 329-333.

Ferrario, et al., (1998), J. Am. Soc. Nephrol, "Novel angiotensin peptides regulate blood pressure, endothelial function, and natriuresis", vol. 9, pp. 1716-1722.

Iyer, et al., (1998), Hypertension, "Vasodepressor actions of angiotensin—(1-7) unmasked during combined treatment with lisinopril and losartan", vol. 31, pp. 699-705.

Freeman, et al., (1996), Hypertension, "Angiotensin-(1-7) inhibits vascular smooth muscle cell growth", vol. 28 (1), pp. 104-108.

Ambühl, et al., (1994), Brain Res. Bull., "[7-D-ALA]-Angiotensin-(1-7): Selective antagonism of angiotensin-(1-7) in the rat paraventricular nucleus", vol. 35 (4), pp. 289-291.

Ferrario, et al., (1997), Hypertension, "Counterregulatory actions of angiotensin-(1-7)", vol. 30, pp. 535-541.

Strawn, et al., (1999), Hypertension, "Angiotensin-(1-7) reduces smooth muscle growth after vascular injury", vol. 33, pp. 207-211.

Mueck, et al., (1999), Int. J. Clin. Pharmacol. Ther., "Valsartan inhibits angiotensin II-stimulated proliferation of smooth muscle cells from human coronary artery", vol. 37(7), pp. 365-366.

Hii, et al., (1998), Br. J. Cancer, "Captopril inhibits tumour growth in a xenograft model of human renal cell carcinoma", vol. 77(6), pp. 880-883.

Small Jr., et al., (1997), Breast Cancer Res. Treat., "Captopril modulates hormone receptor concentration and inhibits proliferation of human mammary ductal carcinoma cells in culture", vol. 44(3), pp. 217-224.

Reddy, et al., (1995), Proc. Soc. Exp. Biol. Med., "Inhibitors of angiotensin-converting enzyme modulate mitosis and gene expression in pancreatic cancer cells", vol. 210(3), pp. 221-226.

Kunert-Radek and Pawlikowski, (1992), "Angiotensin II stimulation of the rat pituitary tumoral cell proliferation *in vitro*", Biochem. Biophys. Res. Commun., vol. 183(1), pp. 27-30.

Speth and Kim, (1990), BBRC, "Discrimination of two angiotensin II receptor subtypes with a selective agonist analogue of angiotensin II, p-aminophenylalanine$^6$ angiotensin II", vol. 169 (3), pp. 997-1006.

Catalioto, et al., (1994), Eur. J. Pharmacol., "Angiotensins induce the release of prostacyclin from rabbit vas deferens: evidence for receptor heterogeneity", vol. 256, pp. 93-97.

Bryson, et al., (1992), Eur. J. Pharmacol., Induction of the angiotensin $AT_2$ receptor subtype expression by differentiation of the neuroblastoma X glioma hybrid, NG-108-15, vol. 225, pp. 119-127.

Janiak, et al., (1992), Hypertension, "Role of angiotensin subtype 2 receptor in neointima formation after vascular injury", vol. 20 (6), pp. 737-745.

Prescott, et al., (1991), Am. J. Pathol., "Angiotensin-converting enzyme inhibitor versus angiotensin II, $AT_1$ receptor antagonist", vol. 139 (6), pp. 1291-1296.

Kauffman, et al., (1991), Life Sci., "Losartan, a nonpeptide angiotensin II (ANGII) receptor antagonist, inhibits neointima formation following balloon injury to rat carotid arteries", vol. 49 (25), pp. PL223-PL228.

Viswanathan, et al., (1992), Peptides, "Expression of angiotensin II $AT_2$ receptors in the rat skin during experimental wound healing", vol. 13, pp. 783-786.

Kumura, et al., (1992), BBRC, "Changes in skin angiotensin II receptors in rats during wound healing", vol. 187 (2), pp. 1083-1090.

Regoli, et al., (1974), Pharmacological Reviews, "Pharmacology of angiotensin", vol. 26 (3), p. 69.

Langer, (1990), Science, "New methods of drug delivery", vol. 249, p. 1527.

* cited by examiner

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence:AII

<400> SEQUENCE: 1

Asp Arg Val Tyr Ile His Pro Phe
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:AII (2-8)

<400> SEQUENCE: 2

Arg Val Tyr Ile His Pro Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:AII (3-8)

<400> SEQUENCE: 3

Val Tyr Ile His Pro Phe
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence:AII (1-7)

<400> SEQUENCE: 4
```

```
Asp Arg Val Tyr Ile His Pro
  1               5
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:AII (2-7)

<400> SEQUENCE: 5

```
Arg Val Tyr Ile His Pro
  1               5
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:AII (3-7)

<400> SEQUENCE: 6

```
Val Tyr Ile His Pro
  1               5
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:AII (5-8)

<400> SEQUENCE: 7

```
Ile His Pro Phe
  1
```

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:AII (1-6)

<400> SEQUENCE: 8

```
Asp Arg Val Tyr Ile His
  1               5
```

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence:AII (1-5)

<400> SEQUENCE: 9

```
Asp Arg Val Tyr Ile
  1               5
```

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:AII (1-4)

<400> SEQUENCE: 10

```
Asp Arg Val Tyr
  1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:AII (1-3)

<400> SEQUENCE: 11

Asp Arg Val
  1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (2)
<223> OTHER INFORMATION: Nle

<400> SEQUENCE: 12

Arg Xaa Tyr Ile His Pro Phe
  1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:AII analogue
<220> FEATURE:
<221> NAME/KEY: MOD_RES
<222> LOCATION: (4)
<223> OTHER INFORMATION: Nle

<400> SEQUENCE: 13

Arg Val Tyr Xaa His Pro Phe
  1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence:AII (6-8)

<400> SEQUENCE: 14

His Pro Phe
  1

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:AII (4-8)

<400> SEQUENCE: 15

Tyr Ile His Pro Phe
  1               5

<210> SEQ ID NO 16
<211> LENGTH: 7
```

```
<212> TYPE: PRT
<213> ORGANISM: Artificial Sequence
<220> FEATURE:
<223> OTHER INFORMATION: Description of Artificial Sequence:AII analogue
      class
<220> FEATURE:
<221> NAME/KEY: UNSURE
<222> LOCATION: (1)
<223> OTHER INFORMATION: Xaa at position 1 can be Arg, Lys, Ala, Orn,
      Ser, MeGly, D-Arg, or D-Lys
<220> FEATURE:
<221> NAME/KEY: UNSURE
<222> LOCATION: (2)
<223> OTHER INFORMATION: Xaa at position 2 can be Val, Ala, Leu, Nle,
      Ile, Gly, Pro, Aib, Acp, or Tyr
<220> FEATURE:
<221> NAME/KEY: UNSURE
<222> LOCATION: (4)
<223> OTHER INFORMATION: Xaa at position 4 can be Ile, Ala, Leu, Nle,
      Val, or Gly

<400> SEQUENCE: 16

Xaa Xaa Tyr Xaa His Pro Phe
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 17

Arg Val Tyr Gly His Pro Phe
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:AII analogue

<400> SEQUENCE: 18

Arg Val Tyr Ala His Pro Phe
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:AII analogue
      1

<400> SEQUENCE: 19

Asp Arg Val Tyr Val His Pro Phe
 1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:AII analogue
      2

<400> SEQUENCE: 20

Asn Arg Val Tyr Val His Pro Phe
 1               5
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:AII analogue 3

<400> SEQUENCE: 21

Ala Pro Gly Asp Arg Ile Tyr Val His Pro Phe
 1               5                  10

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:AII analogue 4

<400> SEQUENCE: 22

Glu Arg Val Tyr Ile His Pro Phe
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:AII analogue 5

<400> SEQUENCE: 23

Asp Lys Val Tyr Ile His Pro Phe
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:AII analogue 6

<400> SEQUENCE: 24

Asp Arg Ala Tyr Ile His Pro Phe
 1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:AII analogue 7

<400> SEQUENCE: 25

Asp Arg Val Thr Ile His Pro Phe
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:AII analogue 8

```
<400> SEQUENCE: 26

Asp Arg Val Tyr Leu His Pro Phe
 1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:AII analogue
      9

<400> SEQUENCE: 27

Asp Arg Val Tyr Ile Arg Pro Phe
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:AII analogue
      10

<400> SEQUENCE: 28

Asp Arg Val Tyr Ile His Ala Phe
 1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:AII analogue
      11

<400> SEQUENCE: 29

Asp Arg Val Tyr Ile His Pro Tyr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:AII analogue
      12

<400> SEQUENCE: 30

Pro Arg Val Tyr Ile His Pro Phe
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:AII analogue
      13

<400> SEQUENCE: 31

Asp Arg Pro Tyr Ile His Pro Phe
 1               5

<210> SEQ ID NO 32
<211> LENGTH: 8
```

```
<212> TYPE: PRT
<213> ORGANISM: Artificial Sequence
<220> FEATURE:
<223> OTHER INFORMATION: Description of Artificial Sequence:AII analogue
      14
<220> FEATURE:
<221> NAME/KEY: MOD_RES
<222> LOCATION: (4)
<223> OTHER INFORMATION: PHOSPHORYLATION

<400> SEQUENCE: 32

Asp Arg Val Tyr Ile His Pro Phe
 1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence:AII analogue
      15
<220> FEATURE:
<221> NAME/KEY: MOD_RES
<222> LOCATION: (3)
<223> OTHER INFORMATION: Nle

<400> SEQUENCE: 33

Asp Arg Xaa Tyr Ile His Pro Phe
 1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence:AII analogue
      16
<220> FEATURE:
<221> NAME/KEY: MOD_RES
<222> LOCATION: (5)
<223> OTHER INFORMATION: Nle

<400> SEQUENCE: 34

Asp Arg Val Tyr Xaa His Pro Phe
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:AII analogue
      17
<220> FEATURE:
<221> NAME/KEY: MOD_RES
<222> LOCATION: (4)
<223> OTHER INFORMATION: homo Ser

<400> SEQUENCE: 35

Asp Arg Val Ser Tyr Ile His Pro Phe
 1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial
      Sequence:p-aminophenylalanine 6 AII
<220> FEATURE:
<221> NAME/KEY: MOD_RES
```

```
<222> LOCATION: (6)
<223> OTHER INFORMATION: p-aminophenylalanine

<400> SEQUENCE: 36

Asp Arg Val Tyr Ile Xaa Pro Phe
 1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence:angiotensin
      I

<400> SEQUENCE: 37

Asp Arg Val Tyr Ile His Pro Phe His Leu
 1               5                  10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence:
      1GD:Ala4-AII(1-7)

<400> SEQUENCE: 38

Asp Arg Val Ala Ile His Pro
 1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: 2GD
      Pro3-AII(1-7)

<400> SEQUENCE: 39

Asp Arg Pro Tyr Ile His Pro
 1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: 5GD Lys
      3-AII(1-7)

<400> SEQUENCE: 40

Asp Arg Lys Tyr Ile His Pro
 1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: 9GD
      Norleu-AII(1-7)
<220> FEATURE:
<221> NAME/KEY: MOD_RES
<222> LOCATION: (3)
<223> OTHER INFORMATION: Nle

<400> SEQUENCE: 41
```

```
Asp Arg Xaa Tyr Ile His Pro
 1               5
```

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence GSD28
      Ile8-AII

<400> SEQUENCE: 42

```
Asp Arg Val Tyr Ile His Pro Ile
 1               5
```

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence:
      Ala3aminoPhe6-AII
<220> FEATURE:
<221> NAME/KEY: MOD_RES
<222> LOCATION: (6)
<223> OTHER INFORMATION: aminophenylalanine

<400> SEQUENCE: 43

```
Asp Arg Ala Tyr Ile Xaa Pro Phe
 1               5
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Ala3-AIII

<400> SEQUENCE: 44

```
Arg Val Ala Ile His Pro Phe
 1               5
```

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence:Gly1-AII

<400> SEQUENCE: 45

```
Gly Arg Val Tyr Ile His Pro Phe
 1               5
```

<210> SEQ ID NO 46
<211> LENGTH: 8
<212> TYPE: PRT
<213> ORGANISM: Artificial Sequence
<220> FEATURE:
<221> NAME/KEY: MOD_RES
<222> LOCATION: (4)
<223> OTHER INFORMATION: Nle
<220> FEATURE:
<223> OTHER INFORMATION: Description of Artificial Sequence:
      Norleu4-AIII

<400> SEQUENCE: 46

```
Arg Val Tyr Xaa Leu His Pro Phe
 1               5
```

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Acpc3-AII
<220> FEATURE:
<221> NAME/KEY: MOD_RES
<222> LOCATION: (3)
<223> OTHER INFORMATION: 1-aminocyclopentane carboxylic acid

<400> SEQUENCE: 47

Asp Arg Xaa Tyr Ile His Pro Phe
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Orn2-AII
<220> FEATURE:
<221> NAME/KEY: MOD_RES
<222> LOCATION: (2)
<223> OTHER INFORMATION: Orn

<400> SEQUENCE: 48

Asp Xaa Val Tyr Ile His Pro Phe
 1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Citron2-AII
<220> FEATURE:
<221> NAME/KEY: MOD_RES
<222> LOCATION: (2)
<223> OTHER INFORMATION: Citron

<400> SEQUENCE: 49

Asp Xaa Val Tyr Ile His Pro Phe
 1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence:
    Pro3Ala4-AII(1-7)

<400> SEQUENCE: 50

Asp Arg Pro Ala Ile His Pro
 1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: 8GD
<220> FEATURE:

```
-continued

<221> NAME/KEY: MOD_RES
<222> LOCATION: (3)
<223> OTHER INFORMATION: Hydroxy Pro

<400> SEQUENCE: 51

Asp Arg Xaa Ala Ile His Pro Phe
 1               5
```

METHODS FOR INHIBITING TUMOR CELL PROLIFERATION

CROSS REFERENCE

This application claims priority to U.S. Provisional Patent Application Ser. No. 60/287,760 filed May 1, 2001.

FIELD OF THE INVENTION

This present invention relates to compositions and methods useful for the inhibition of tumor cell proliferation.

BACKGROUND OF THE INVENTION

Despite many years of promising new therapies, cancer remains a major cause of morbidity and mortality (Bailar et al., N. Engl. J. Med. 336:1569–1574, 1997). Typical therapeutic treatments may include surgery, radiation therapy, and/or chemotherapy. A variety of chemotherapeutic compounds have found widespread use in the clinical treatment of cancer and have proven to be indispensable in the effort to combat this disease. Nevertheless, on an individual case basis, some cancers can respond differently to a given therapy making it difficult and costly to achieve an effective clinical treatment regimen. Accordingly, there is a substantial need for new methods and active agents that are effective in inhibiting the growth of tumors.

SUMMARY OF THE INVENTION

The present invention provides methods for inhibiting tumor cell proliferation by administering to a patient in need thereof an amount effective of angiotensinogen, angiotensin I (AI), AI analogues, AI fragments and analogues thereof, angiotensin II (AII), AII analogues, AII fragments or analogues thereof or AII $AT_2$ type 2 receptor agonists, either alone, combined, or in further combination with known therapeutic methods for inhibiting tumor cell proliferation, such as surgery, cytokine therapy, hormone therapy, and anti-hormone therapy. In a preferred embodiment, the tumor comprises an adenocarcinoma. In a further preferred embodiment, the tumor comprises an adenocarcinoma of ovarian, endometrial, uterine, or breast origin.

DETAILED DESCRIPTION OF THE PREFERRED EMBODIMENTS

Unless otherwise indicated, the term "angiotensin converting enzyme inhibitors" or "ACE inhibitors" includes any compound that inhibits the conversion of the decapeptide angiotensin I to angiotensin II, and include but are not limited to alacepril, alatriopril, altiopril calcium, ancovenin, benazepril, benazepril hydrochloride, benazeprilat, benzazepril, benzoylcaptopril, captopril, captopril-cysteine, captopril-glutathione, ceranapril, ceranopril, ceronapril, cilazapril, cilazaprilat, converstatin, delapril, delapril-diacid, enalapril, enalaprilat, enalkiren, enapril, epicaptopril, foroxymithine, fosfenopril, fosenopril, fosenopril sodium, fosinopril, fosinopril sodium, fosinoprilat, fosinoprilic acid, glycopril, hemorphin-4, idapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. (See for example Jackson, et al., Renin and Angiotensin in Goodman & Gilman's The Pharmacological Basis of Therapeutics, 9th ed., eds. Hardman, et al. (McGraw Hill, 1996); and U.S. Pat. No. 5,977,159).

Unless otherwise indicated, the term "active agents" as used herein refers to the group of compounds comprising angiotensinogen, angiotensin I (AI), AI analogues, AI fragments and analogues thereof, angiotensin II (AII), AII analogues, AII fragments or analogues thereof or AII $AT_2$ type 2 receptor agonists, either alone, combined, or in further combination with other compounds, for inhibiting tumor cell proliferation.

As used herein, the term "tumor" includes refers to tumor types including but not limited to carcinomas, which as used herein refers to tumors originating in the epithelial cells of an organ. In a preferred embodiment, the tumor type is an adenocarcinoma, which as used herein refers to a subclass of carcinomas that originate in a glandular portion of an organ. In a more preferred embodiment, the organ in which the adenocarcinoma originates is selected from the group consisting of ovarian, endometrial, uterine, and breast tissues, most preferably from endometrial or breast tissue.

While not being limited in any way by a mechanism of action of the active agents in inhibiting tumor cell proliferation, it is proposed that the active agents may be more active inhibiting proliferation of hormone-dependent tumors, including but not limited to those of ovarian, endometrial, uterine, and breast origin.

As used herein, the term "amount effective to inhibit tumor cell proliferation" is taken to mean an appropriate quantity of one or more active agents, that when administered to a subject in need thereof, results in a slowing or stopping of the rate of progression of tumor cell growth, and/or that decreases the size of a pre-existing tumor in a subject. The active agents thus act as chemotherapeutic agents for inhibiting tumor cell proliferation and tumor growth in a patient in need thereof, and thus further chemotherapeutic agents are not needed.

U.S. Pat. No. 5,015,629 to DiZerega (the entire disclosure of which is hereby incorporated by reference) describes a method for increasing the rate of healing of wound tissue, comprising the application to such tissue of angiotensin II (AII) in an amount which is sufficient for said increase. The application of AII to wound tissue significantly increases the rate of wound healing, leading to a more rapid re-epithelialization and tissue repair. The term AII refers to an octapeptide present in humans and other species having the sequence Asp-Arg-Val-Tyr-Ile-His-Pro-Phe [SEQ ID NO:1]. The biological formation of angiotensin is initiated by the action of renin on the plasma substrate angiotensinogen (*Circulation Research* 60:786–790 (1987); Clouston et al., *Genomics* 2:240–248 (1988); Kageyama et al., *Biochemistry* 23:3603–3609; Ohkubo et al., *Proc. Natl. Acad. Sci.* 80:2196–2200 (1983)); all references hereby incorporated in their entirety). The substance so formed is a decapeptide called angiotensin I (AI) which is converted to AII by the converting enzyme angiotensinase which removes the C-terminal His-Leu residues from AI, Asp-Arg-Val-Tyr-Ile-His-Pro-Phe-His-Leu [SEQ ID NO:37]. AII is a known pressor agent and is commercially available.

Studies have shown that AII increases mitogenesis and chemotaxis in cultured cells that are involved in wound repair, and also increases their release of growth factors and extracellular matrices (diZerega, U.S. Pat. No. 5,015,629; Dzau et. al., *J. Mol. Cell. Cardiol.* 21:S7 (Supp III) 1989;

Berk et. al., *Hypertension* 13:305–14 (1989); Kawahara, et al., *BBRC* 150:52–9 (1988); Naftilan, et al., *J. Clin. Invest.* 83:1419–23 (1989); Taubman et al., *J. Biol. Chem.* 264: 526–530 (1989); Nakahara, et al., *BBRC* 184:811–8 (1992); Stouffer and Owens, *Circ. Res.* 70:820 (1992); Wolf, et al., *Am. J. Pathol.* 140:95–107 (1992); Bell and Madri, *Am. J. Pathol.* 137:7–12 (1990)). In addition, AII was shown to be angiogenic in rabbit corneal eye and chick chorioallantoic membrane models (Fernandez, et al., *J. Lab. Clin. Med.* 105:141 (1985); LeNoble, et al., Eur. J. Pharmacol. 195: 305–6 (1991)).

We have previously demonstrated that angiotensinogen, angiotensin I (AI), AI analogues, AI fragments and analogues thereof, angiotensin II (AII), AII analogues, AII fragments or analogues thereof; AII $AT_2$ type 2 receptor agonists are effective in accelerating wound healing, the proliferation of certain cell types, and are effective when used as adjuncts to chemotherapy or radiation therapy to treat patients in need of such treatment. See, for example, co-pending U.S. patent application Ser. No. 08/126,370, filed Sep. 24, 1993; Ser. No. 09/208,337, filed Dec. 9, 1998; Ser. Nos. 09/108,478, 09/434,746 filed Nov. 5, 1999; Ser. No. 09/503,872, filed Feb. 14, 2000; Ser. No. 08/990,664, filed Dec. 15, 1997; Ser. No. 09/210,249, filed Dec. 11, 1998; Ser. No. 09/098,806, filed Nov. 24, 1998; Ser. No. 09/012,400, filed Jan. 23, 1998; Ser. No. 09/264,563, filed Mar. 8, 1999; Ser. No. 09/287,674, filed Apr. 7, 1999; Ser. No. 09/307,940, filed May 10, 1999; Ser. No. 09/246,162, filed Feb. 8, 1999; Ser. No. 09/255,136, filed Feb. 19, 1999; Ser. No. 09/245,680, filed Feb. 8, 1999; Ser. No. 09/250,703, filed Feb. 15, 1999; Ser. No. 09/246,525, filed Feb. 8, 1999; Ser. No. 09/266,293, filed Mar. 11, 1999; Ser. No. 09/332,582, filed Jun. 14, 1999; Ser. No. 09/373,962, filed Aug. 13, 1999; Ser. No. 09/352,191, filed Jul. 12, 1999; as well as issued U.S. Pat. Nos. 5,015,629; 5,629,292; 5,716,935; 5,834,432; 5,955,430; 6,096,709; 6,110,895; 6,165,978; and 6,177,407.

The effect of AII on a given cell type has been hypothesized to be dependent, in part, upon the AII receptor subtypes the cell expresses (Shanugam et al., *Am. J. Physiol.* 268:F922–F930 (1995); Helin et al., *Annals of Medicine* 29:23–29 (1997); Bedecs et al., *Biochem J.* 325:449–454 (1997)). These studies have shown that AII receptor subtype expression is a dynamic process that changes during development, at least in some cell types. AII activity is typically modulated by either or both the AT1 and AT2 AII receptors. However, AII has recently been shown to stimulate proliferation of primary human keratinocytes via a non-AT1, non-AT2 receptor. (Steckelings et al., Biochem. Biophys. Res. Commun. 229:329–333 (1996)). These results underscore the cell-type (ie: based on receptor expression) specific nature of AII activity.

Many studies have focused upon AII(1-7) (AII residues 1-7) (SEQ ID NO:4) or other fragments of AII to evaluate their activity. These studies suggest that the AII fragment AII(1-7) acts through one or more receptors that are distinct from the AT1 and AT2 receptors that modulate AII activity. (Ferrario et al., J. Am. Soc. Nephrol. 9:1716–1722 (1998); Iyer et al., Hypertension 31:699–705 (1998); Freeman et al., Hypertension 28:104 (1996); Ambuhl et al., Brain Res. Bull. 35:289 (1994)). Thus, AII(1-7) activity on a particular cell type cannot be predicted based solely on the effect of AII on the same cell type. In fact, there is evidence that AII(1-7) often opposes the actions of AII. (See, for example, Ferrario et al., Hypertension 30:535–541 (1997))

AII(1-7) (SEQ ID NO:4) has been shown to inhibit smooth muscle cell proliferation, and to reduce smooth muscle cell growth after vascular injury (Strawn et al., Hypertension 33:207–211 (1999)). A(II), in contrast, is known to increase proliferation of smooth muscle cells (Mueck, et al., Int. J. Clin. Pharmacol. Ther., 37(7):365–6 (1999)).

The ACE inhibitor captopril has been shown to have antitumor activity in a xenograft mouse model of human renal cell carcinoma, although proliferation of renal carcinoma cells in vitro was not inhibited by captopril (Hii et al., Br. J. Cancer 77(6):880–83 (1998)). Similar in vitro studies have demonstrated that captopril can inhibit proliferation of human mammary ductal carcinoma cells (Small Jr., et al., Breast Cancer Res. Treat., 44(3):217–24 (1997)) as well as hamster pancreatic duct carcinoma cells (Reddy, et al., Proc. Soc. Exp. Biol. Med., 210(3):221–6 (1995)).

Clinical treatments employing AII in combination with chemotherapeutic agents such as mitomycin C and 5-FU (5-fluorouracil), have been used against liver metastasis from gastric cancer, but were not effective in controlling recurrences of metastatic growth (Iwasaki et al., Gan To Kagaku Ryoho 22(11):1674–78 (1995); Iwasaki et al., Gan To Kagaku Ryoho 25(9):1412–15 (1998); Ohashi et al., Gan To Kagaku Ryoho 26(12):1777–80 (1999)). AII has been shown to increase rat pituitary tumor cell proliferation in vitro (Kunert-Radek and Pawlikowski, Biochem. Biophys. Res. Commun., 183(1):27–30 (1992)).

Based on the above, there would be no expectation by one of skill in the art that the active agents of the present invention could be used to treat and prevent tumor cell proliferation.

A peptide agonist selective for the AT2 receptor (AII has 100 times higher affinity for AT2 than AT1) is p-aminophenylalanine6-AII ["(p-NH$_2$-Phe)6-AII)"], Asp-Arg-Val-Tyr-Ile-Xaa-Pro-Phe [SEQ ID NO.36] wherein Xaa is p-NH$_2$-Phe (Speth and Kim, BBRC 169:997–1006 (1990). This peptide gave binding characteristics comparable to AT2 antagonists in the experimental models tested (Catalioto, et al., *Eur. J. Pharmacol.* 256:93–97 (1994); Bryson, et al., *Eur. J. Pharmacol.* 225:119–127 (1992).

The effects of AII and AII receptor antagonists have been examined in two experimental models of vascular injury and repair which suggest that both AII receptor subtypes (AT1 and AT2) play a role in wound healing (Janiak et al., *Hypertension* 20:737–45 (1992); Prescott, et al., *Am. J. Pathol.* 139:1291–1296 (1991); Kauffman, et al., *Life Sci.* 49:223–228 (1991); Viswanathan, et al., *Peptides* 13:783–786 (1992); Kimura, et al., *BBRC* 187:1083–1090 (1992)).

As hereinafter defined, a preferred class of AT2 agonists for use in accordance with the present invention comprises AII analogues or active fragments thereof having p-NH$_2$-Phe in a position corresponding to a position 6 of AII. In addition to peptide agents, various nonpeptidic agents (e.g., peptidomimetics) having the requisite AT2 agonist activity are further contemplated for use in accordance with the present invention.

The active agents of particular interest in accordance with the present invention comprise a sequence of at least three contiguous amino acids of groups $R^1$–$R^8$ in the sequence of general formula I

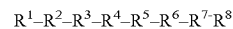

wherein $R^1$ is selected from the group consisting of H, Asp, Glu, Asn, Acpc (1-aminocyclopentane carboxylic acid), Ala, Me$^2$Gly, Pro, Bet, Glu(NH$_2$), Gly, Asp(NH$_2$) and Suc, R² is is selected from the group consisting of Arg, Lys, Ala, Citron, Orn, Ser(Ac), Sar, D-Arg and D-Lys;

R³ is selected from the group consisting of Val, Ala, Leu, norLeu, Ile, Gly, Lys, Pro, HydroxyPro, Aib, Acpc and Tyr;

R⁴ is selected from the group consisting of Tyr, Tyr(PO₃)₂, Thr, Ser, homoSer, azaTyr, and Ala;

R⁵ is selected from the group consisting of Ile, Ala, Leu, norLeu, Val and Gly;

R⁶ is selected from the group consisting of His, Arg or 6-NH₂-Phe;

R⁷ is selected from the group consisting of Pro or Ala; and

R⁸ is selected from the group consisting of Phe, Phe(Br), Ile and Tyr, excluding sequences including R⁴ as a terminal Tyr group.

In alternate embodiments, the active agents comprise a sequence of at least four, five, six, or seven contiguous amino acids of groups R¹–R⁸ in the sequence of general formula I. In a further alternative, the active agents consist of a sequence of at least four, five, six, or seven contiguous amino acids of groups R¹–R⁸ in the sequence of general formula I.

Compounds falling within the category of AT2 agonists useful in the practice of the invention include the AII analogues set forth above subject to the restriction that R⁶ is p-NH₂-Phe.

Particularly preferred combinations for R¹ and R² are Asp-Arg, Asp-Lys, Glu-Arg and Glu-Lys. Particularly preferred embodiments of this class comprise the following amino acid sequences: AII [SEQ ID NO:1]; AIII or AII(2-8), Arg-Val-Tyr-Ile-His-Pro-Phe [SEQ ID NO:2]; AII(3-8), also known as des1-AIII or AIV, Val-Tyr-Ile-His-Pro-Phe [SEQ ID NO:3]; AII(1-7), Asp-Arg-Val-Tyr-Ile-His-Pro [SEQ ID NO:4]; AII(2-7), Arg-Val-Tyr-Ile-His-Pro [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ ID NO:9]; AII(1-4), Asp-Arg-Val-Tyr [SEQ ID NO:10]; and AII(1-3), Asp-Arg-Val [SEQ ID NO:11]. Other preferred embodiments include: Arg-norLeu-Tyr-Ile-His-Pro-Phe [SEQ ID NO:12] and Arg-Val-Tyr-norLeu-His-Pro-Phe [SEQ ID NO:13]. Still another preferred embodiment encompassed within the scope of the invention is a peptide having the sequence Asp-Arg-Pro-Tyr-Ile-His-Pro-Phe [SEQ ID NO:31]. AII(4-8), Tyr-Ile-His-Pro-Phe [SEQ ID NO:15] was also tested and found not to be effective.

Another class of compounds of particular interest in accordance with the present invention are those of the general formula II

R²–R³–R⁴–R⁵–R⁶–R⁷–R⁸ in which R² is selected from the group consisting of H, Arg, Lys, Ala, Orn, Citron, Ser(Ac), Sar, D-Arg and D-Lys;

R³ is selected from the group consisting of Val, Ala, Leu, norLeu, Ile, Gly, Pro, Hydroxy-Pro, Aib, Acpc and Tyr;

R⁴ is selected from the group consisting of Tyr, Tyr(PO₃)₂, Thr, Ser, homoSer, azaTyr, and Ala;

R⁵ is selected from the group consisting of Ile, Ala, Leu, norLeu, Val and Gly;

R⁶ is His, Arg or 6-NH₂-Phe;

R⁷ is Pro or Ala; and

R⁸ is selected from the group consisting of Phe, Phe(Br), Ile and Tyr.

A particularly preferred subclass of the compounds of general formula II has the formula R²–R³-Tyr-R⁵-His-Pro-Phe [SEQ ID NO:16]

wherein R², R³ and R⁵ are as previously defined. Particularly preferred compounds include peptides having the structures Arg-Val-Tyr-Gly-His-Pro-Phe [SEQ ID NO:17] and Arg-Val-Tyr-Ala-His-Pro-Phe [SEQ ID NO:18]. The fragment AII(4-8) was ineffective in repeated tests; this is believed to be due to the exposed tyrosine on the N-terminus.

Other particularly preferred embodiments include:

| | | | |
|---|---|---|---|
| 1GD | Ala4-AII(1–7) | DRVAIHP | SEQ ID NO:38 |
| 2GD | Pro3-AII(1–7) | DRPYIHP | SEQ ID NO:39 |
| 5GD | Lys3-AII(1–7) | DRKYIHP | SEQ ID NO:40 |
| 9GD | NorLeu-AII(1–7) | DR(nor)YIHP | SEQ ID NO:41 |
| GSD 28 | Ile⁸-AII | DRVYIHPI | SEQ ID NO:42 |
| | Ala3aminoPhe6 AIII | DRAYIF*PF | SEQ ID NO:43 |
| | Ala3-AIII | RVAIHPF | SEQ ID NO:44 |
| | Gly¹-AII | GRVYIHPF | SEQ ID NO:45 |
| | NorLeu⁴-AIII | --RVYnLHPF | SEQ ID NO:46 |
| | Acpc³-AII | DR(Acpc)YIHPF | SEQ ID NO:47 |
| GSD 37B | Orn²-AII | D(Orn)VYIHPF | SEQ ID NO:48 |
| GSD 38B | Citron²-AII | D(Citron)VYIHPF | SEQ ID NO:49 |
| 3GD | Pro³Ala⁴-AII(1–7) | DRPAIHP | SEQ ID NO:50 |
| 8GD | Hydroxy-Pro³-AII(1–7) | DRP(OH)AIHP | SEQ ID NO:51 |

Thus, in further embodiments of the invention, the active agents comprise an amino acid sequence selected from the group consisting of any one of SEQ ID NOS:1–51. In an farther embodiment, the active agent does not consist of AII (SEQ ID NO:1). In a further embodiment, the active agent comprises the amino acid sequence of SEQ ID NO:4 (AII (1-7)). In a further embodiment, the active agent consists of the amino acid sequence of any of SEQ ID NOS:1–51. In a further preferred embodiment, the active agent consists of the amino acid of SEQ ID NO:4.

In the above formulas, the standard three-letter abbreviations for amino acid residues are employed. In the absence of an indication to the contrary, the L-form of the amino acid is intended. Other residues are abbreviated as follows:

TABLE 1

Abbreviation for Amino Acids

| | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |
| Sar | N-methylglycyl (sarcosine) |
| Cit | Citron |
| Orn | Ornithine |

It has been suggested that AII and its analogues adopt either a gamma or a beta turn (Regoli, et al., *Pharmacological Reviews* 26:69 (1974). In general, it is believed that neutral side chains in position $R^3$, $R^5$ and $R^7$ may be involved in maintaining the appropriate distance between active groups in positions $R^4$, $R^6$ and $R^8$ primarily responsible for binding to receptors and/or intrinsic activity. Hydrophobic side chains in positions $R^3$, $R^5$ and $R^8$ may also play an important role in the whole conformation of the peptide and/or contribute to the formation of a hypothetical hydrophobic pocket.

Appropriate side chains on the amino acid in position $R^2$ may contribute to affinity of the compounds for target receptors and/or play an important role in the conformation of the peptide. For this reason, Arg and Lys are particularly preferred as $R^2$. Alternatively, $R_2$ may be H, Ala, Orn, Citron, Ser(Ac), Sar, D-Arg, or D-Lys.

For purposes of the present invention, it is believed that $R^3$ may be involved in the formation of linear or nonlinear hydrogen bonds with $R^5$ (in the gamma turn model) or $R^6$ (in the beta turn model). $R^3$ would also participate in the first turn in a beta antiparallel structure (which has also been proposed as a possible structure). In contrast to other positions in general formula I, it appears that beta and gamma branching are equally effective in this position. Moreover, a single hydrogen bond may be sufficient to maintain a relatively stable conformation. Accordingly, $R^3$ may suitably be selected from Lys, Val, Ala, Leu, norLeu, Ile, Gly, Pro, Hydroxy-Pro, Aib, Acpc and Tyr.

With respect to $R^4$, conformational analyses have suggested that the side chain in this position (as well as in $R^3$ and $R^5$) contribute to a hydrophobic cluster believed to be essential for occupation and stimulation of receptors. Thus, $R^4$ is preferably selected from Tyr, Thr, Tyr $(PO_3)_2$, homoSer, Ser and azaTyr. In this position, Tyr is particularly preferred as it may form a hydrogen bond with the receptor site capable of accepting a hydrogen from the phenolic hydroxyl (Regoli, et al. (1974), supra). It has also been found that $R^4$ can be Ala.

In position $R^5$, an amino acid with a β aliphatic or alicyclic chain is particularly desirable. Therefore, while Gly is suitable in position $R^5$, it is preferred that the amino acid in this position be selected from Ile, Ala, Leu, norLeu, and Val.

In position $R^6$, His, Arg or 6-$NH_2$-Phe are preferred. The unique properties of the imidazole ring of histidine (e.g., ionization at physiological pH, ability to act as proton donor or acceptor, aromatic character) are believed to contribute to its particular utility as $R^6$. For example, conformational models suggest that His may participate in hydrogen bond formation (in the beta model) or in the second turn of the antiparallel structure by influencing the orientation of $R^7$. Similarly, it is presently considered that $R^7$ should be Pro or Ala in order to provide the most desirable orientation of $R^8$. In position $R^8$, both a hydrophobic ring and an anionic carboxyl terminal appear to be particularly useful in binding of the analogues of interest to receptors; therefore, Tyr, Ile, Phe(Br), and especially Phe are preferred for purposes of the present invention.

Other active agents of particular interest include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 19 |
| Analogue 2 | Asn-Arg-Val-Tyr-Val-His-Pro-Phe | SEQ ID NO: 20 |
| Analogue 3 | Ala-Pro-Gly-Asp-Arg-Ile-Tyr-Val-His-Pro-Phe | SEQ ID NO: 21 |
| Analogue 4 | Glu-Arg-Val-Tyr-Ile-His-Pro-Phe | SEQ ID NO: 22 |
| Analogue 5 | Asp-Lys-Val-Tyr-Ile-His-Pro-Phe | SEQ ID NO: 23 |
| Analogue 6 | Asp-Arg-Ala-Tyr-Ile-His-Pro-Phe | SEQ ID NO: 24 |
| Analogue 7 | Asp-Arg-Val-Thr-Ile-His-Pro-Phe | SEQ ID NO: 25 |
| Analogue 8 | Asp-Arg-Val-Tyr-Leu-His-Pro-Phe | SEQ ID NO: 26 |
| Analogue 9 | Asp-Arg-Val-Tyr-Ile-Arg-Pro-Phe | SEQ ID NO: 27 |
| Analogue 10 | Asp-Arg-Val-Tyr-Ile-His-Ala-Phe | SEQ ID NO: 28 |

TABLE 2-continued

Angiotensin II Analogues

| Analogue Name | Amino Acid Sequence | All Analogue Sequence Identifier |
|---|---|---|
| Analogue 11 | Asp-Arg-Val-Tyr-Ile-His-Pro-Tyr | SEQ ID NO: 29 |
| Analogue 12 | Pro-Arg-Val-Tyr-Ile-His-Pro-Phe | SEQ ID NO: 30 |
| Analogue 13 | Asp-Arg-Pro-Tyr-Ile-His-Pro-Phe | SEQ ID NO: 31 |
| Analogue 14 | Asp-Arg-Val-Tyr(PO$_3$)$_2$-Ile-His-Pro-Phe | SEQ ID NO: 32 |
| Analogue 15 | Asp-Arg-norLeu-Tyr-Ile-His-Pro-Phe | SEQ ID NO: 33 |
| Analogue 16 | Asp-Arg-Val-Tyr-norLeu-His-Pro-Phe | SEQ ID NO: 34 |
| Analogue 17 | Asp-Arg-Val-homoSer-Tyr-Ile-His-Pro-Phe | SEQ ID NO: 35 |

The polypeptides of the instant invention may be synthesized by any conventional method, including, but not limited to, those set forth in J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. The disclosures of the foregoing treatises are incorporated by reference herein.

In general, these methods involve the sequential addition of protected amino acids to a growing peptide chain (U.S. Pat. No. 5,693,616, herein incorporated by reference in its entirety). Normally, either the amino or carboxyl group of the first amino acid and any reactive side chain group are protected. This protected amino acid is then either attached to an inert solid support, or utilized in solution, and the next amino acid in the sequence, also suitably protected, is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

Preferably, peptides are synthesized according to standard solid-phase methodologies, such as may be performed on an Applied Biosystems Model 430A peptide synthesizer (Applied Biosystems, Foster City, Calif.), according to manufacturer's instructions. Other methods of synthesizing peptides or peptidomimetics, either by solid phase methodologies or in liquid phase, are well known to those skilled in the art.

Alternatively, the peptides can be produced by standard molecular biological techniques.

One embodiment the present invention provides for pharmaceutical compositions comprising an effective amount of one or more of the active agents of the present invention to inhibit tumor cell proliferation, in combination with a pharmaceutically acceptable carrier.

In another embodiment, of the present invention provides for a method of inhibiting tumor cell proliferation by contacting tumor cells with an amount effective of one or more of the active agents of the present invention, or pharmaceutical compositions thereof, such that tumor cell proliferation is inhibited.

In yet another embodiment, the present invention provides methods for the inhibition of tumor cell proliferation by administering to a patient in need thereof an amount effective to inhibit tumor cell proliferation of one or more of the active agents or pharmaceutical compositions of the invention, either alone or in further combination with other compounds and methods effective for inhibiting tumor cell proliferation.

In each of these embodiments, it is preferred that the tumor comprises a carcinoma, more preferably an adenocarcinoma. In a more preferred embodiment, the organ in which the adenocarcinoma originates is selected from the group consisting of ovarian, endometrial, uterine, and breast tissues, most preferably from endometrial or breast tissue.

The active agents may be made up in a solid form (including granules, powders or suppositories) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, co-solvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the active agents are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems; crystalloid and viscous instillates; absorbable and/or biodegradable mechanical barriers; and polymeric delivery materials, such as polyethylene oxide/polypropylene oxide block copolymers (e.g. poloxamers), poly-orthoesters, cross-linked polyvinyl alcohol, polyanhydrides, polymethacrylate and polymethacrylamide hydrogels, anionic carbohydrate polymers, etc. Useful delivery systems are well known in the art and are described in, e.g., U.S. Pat. No. 4,937,254, the entire disclosure of which is hereby incorporated by reference.

For use in treating or preventing tumor cell proliferation, the active agents may be administered by any suitable route, including local delivery, parentally, transdermally, or dermally in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally.

Local delivery of the active agents of the invention can be by a variety of techniques that administer the agent at or near the site of neoplastic growth. Examples of site-specific or targeted local delivery techniques are not intended to be limiting but to be illustrative of the techniques available. Examples include local delivery catheters, such as an infusion catheter, an indwelling catheter, or a needle catheter, stets, synthetic grafts, adventitial wraps, shunts and stents or other implantable devices, site specific carriers, direct injection, or direct applications. (U.S. Pat. No. 5,981,568, incorporated by reference herein in its entirety.)

Local delivery by an implant describes the surgical placement of a matrix that contains the active agent into the tumor or immediate surrounding area. The implanted matrix can release the active agent by diffusion, chemical reaction, or solvent activators. See, for example, Lange, Science, 249, 1527 (1990).

Another example is a delivery system in which a polymer that contains the active agent is injected into the area of the tumor in liquid form. The polymer then solidifies or cures to form an implant that is retained in situ. This technique is described in PCT WO 90/03768 (Donn, Apr. 19, 1990), the disclosure of which is incorporated by reference herein.

For topical administration, the active agents may be formulated as is known in the art for direct application to a target area. Conventional forms for this purpose include wound dressings, coated bandages or other polymer coverings, ointments, lotions, pastes, jellies, sprays, and aerosols. The percent by weight of the active agent of the invention present in a topical formulation will depend on various factors, but generally will be from 0.005% to 95% of the total weight of the formulation, and typically 1–25% by weight.

The dosage regimen for treating or preventing tumor cell growth with the active agents is based on a variety of factors, including the age, weight, sex, medical condition of the individual, the severity of the condition, the route of administration, and the particular compound employed. Thus, the dosage regimen may vary widely, but can be determined by a physician. Dosage levels of the order of between 0.1 ng/kg and 10 mg/kg of the active agents per body weight are useful for all methods of use disclosed herein.

In a preferred method of treatment, an amount effective of the active agents or pharmaceutical compositions comprising the active agents to inhibit tumor cell proliferation is administered to a patient in need of such treatment as soon as possible following diagnosis of a tumorigenic growth.

In another aspect of the invention, pharmaceutical compositions are provided that comprise an amount effective to treat or prevent tumor cell proliferation of one or more of the active agents of the invention alone or in combination with other anti-tumor agents, including but not limited to angiotensin converting enzyme inhibitors and angiogenesis inhibitors.

The present invention, by providing methods for treating or preventing tumor cell proliferation is broadly useful to treat or inhibit tumor cell growth. It will be recognized that the active agents and dosage forms (both free and sustained release) of the invention are not restricted in use for therapy following other methods such as surgical excision. Thus, other aspects of the invention include therapeutic conjugates, dosage forms, and protocols useful in sustained therapeutic intervention for reducing, delaying, or eliminating further tumor cell growth.

EXAMPLE 1

Human Tumor Cell Clonigenic Assay Samples 1–30

PURPOSE: The purpose this study is to evaluate the effect of an angiotensin peptide, AII(1-7) (SEQ ID NO:4) on human tumor cell proliferation.

TEST SYSTEM:

| | |
|---|---|
| Species: | Human, discarded primary tumors |
| Parameters Measured: | Tumor Cell Proliferation |
| Test Article: | AII(1–7), 0.1 ng/ml–10 µg/ml ($1.1 \times 10^{-10}$ to $1.1 \times 10^{-5}$ M) |

Methods

Tumor Cell Preparation

Primary and metastatic tumors obtained from the Department of Obstetrics and Gynecology Pathology Section and the Surgical Pathology Division of Los Angeles County/University of Southern California were minced into pieces less than 2 mm in diameter in the presence of RPMI-1640 (Gibco, Grand Island, NTY) containing 15% heat-inactivated fetal calf serum. Each gram of tumor tissue was treated with 10–20 mL of enzyme medium, consisting of Hanks' balanced salt solution with 0.03% DNAse (500 Kunitz units/mL; Sigma Chemical Co., St. Louis, Mo.) and 0.14% collagenase type I (Sigma). Tumor fragments were stirred for 90 minutes at 37° C. in the presence of 5% $CO_2$. After enzymatic digestion, the free cells were decanted through 40-gauge mesh strainers and centrifuged at 200×g for 10 minutes. The supernatant was removed and viable cells were resuspended in RPMI 1640. The cell number was determined using a hematocytometer and 0.04% trypan blue dye. The cells were then centrifuged and the pellet resuspended in RPMI 1640 at $5 \times 10^5$ cells/mL.

Tumor Cell Culture

Human cancer cells were obtained from operative specimens provided by the Division of Gynecologic Oncology, Department of Obstetrics and Gynecology, or the Department of Surgical Pathology of Los Angeles County/University of Southern California School of Medicine. Tumor cells were maintained in vitro in RPMI 1640 medium supplemented with 15% heat-inactivated fetal calf serum, 100 μg/mL streptomycin, fungizone 25 μg/mL, and 100 μ/mL penicillin.

Clonigenic Assay

Cells were cultured on an underlayer of 0.5% agarose (Bethesda Research Labs, Bethesda, Md.) prepared from a 3% stock of agarose with added penicillin (100 units/mL), streptomycin (100 μg/mL), and fungizone (1.25 μg/mL) (GIBCO) as per a modification of an established procedure. The cloning efficiency of this assay varied depending upon the source of the tissue. One milliliter of this 0.5% agarose mixture was added to each 16×16-mm well of a 24-well plate and the plates were refrigerated for 10 minutes at 4° C. Cells were suspended in 0.6% agarose in RPMI-1640 supplemented with antibiotics and 15% fetal calf serum. One aliquot (0.5 mL) of cell suspension was added to each underlayer at a final concentration of $5 \times 10^4$ cells/well, and the plates were refrigerated 10 minutes at 4° C.

AII(1-7) (SEQ ID NO:4) was added to samples as an overlayer in 300 μL of RPMI-1640 medium in concentrations from 0.1 ng to 10 μg/well. Positive controls were prepared as above, but the overlayer did not contain AII(1-7). Negative controls were prepared by omitting fetal calf serum from the cell suspension and AII(1-7) from the overlayer. After a 72-hour incubation at 37° C., 5 μCi of tritiated thymidine (specific activity 18.2 Ci/mmol; New England Nuclear, Boston, Mass.) was layered over each well, and the plates were returned to the incubator for an additional 24 hours, incorporation of thymidine was terminated by transferring the agarose layers to 10-mL glass centrifuge tubes (Kimble, Division of Owens, Ill.) and boiling the tubes for 15 minutes in a water bath. The volume was brought to 8 mL, the tubes were centrifuged, and the pellets were washed with phosphate-buffered saline and then dissolved in 3 mL of 0.85 N KOH for 1 hour at 80° C. The tubes were cooled on ice and the hydrolysates were precipitated by adding 30 μL of 1% human serum albumin (Sigma) and 2.4 mL of ice-cold trichloroacetic acid. After overnight storage at 4° C., precipitates were collected by centrifugation. Pellets were washed with 5% trichloroacetic acid, dissolved in 0.3 mL of 0.075 N KOH, and transferred to scintillation vials to which 5 mL of Liquiscint (National Diagnostics, Somerville, N.J.) were added. Radioactivity per vial was measured in a Nuclear-Chicago liquid scintillation counter.

Results

Various tumor types were isolated directly from cancer patients have been obtained and assayed in this clonigenic system. The results are summarized in Table 3 below, and calculated IC50 data for samples in which AII(1-7) decreased proliferation (as well as some negative controls) are presented in Table 4.

TABLE 3

Effect of AII(1–7) on the Proliferation of Selected Human Primary Tumor Cells.

| Sample Number | Effect of AII(1–7) | Diagnosis |
|---|---|---|
| Sample 1 | No Effect | Leiomyosarcoma |
| Sample 2 | Decreased | Ovarian papillary serous carcinoma |
| Sample 3 | No Effect | Ovarian carcinoma-clear cell |
| Sample 4 | Decreased | Endometrial adenocarcinoma |
| Sample 5 | Equivocal | Metastatic uterine carcinosarcoma to the ovary |
| Sample 6 | No Effect | Serous tumor of low malignant potential |
| Sample 7 | Decreased | Breast adenocarcinoma |
| Sample 8 | Decreased | Endometrial adenocarcinoma |
| Sample 9 | Decreased | Endometrial adenocarcinoma |
| Sample 10 | No Effect | Breast adenocarcinoma |
| Sample 11 | No Effect | Endometrial adenocarcinoma |
| Sample 12 | No Effect | Squamous Cell Carcinoma of the Cervix, gr 3 |
| Sample 13 | No Effect | Metastatic Ovarian Papillary Carcinoma to Omentum |
| Sample 14 | No Growth | Squamous Cell Carcinoma of Lung |
| Sample 15 | No Growth | Metastatic Ovarian Papillary Carcinoma |
| Sample 16 | No Effect | Ovarian Cancer-High Grade Clear Cell Carcinoma |
| Sample 17 | No Effect | Uterine Carcinosarcoma |
| Sample 18 | No Effect | Endometrial adenocarcinoma |
| Sample 19 | No Effect | Recurrent moderately differentiated colonic adenocarcinoma |
| Sample 20 | Decreased | Breast adenocarcinoma |
| Sample 21 | No Effect | Breast adenocarcinoma |
| Sample 22 | Decreased | Endometrial adenocarcinoma |
| Sample 23 | Decreased | Endometrial adenocarcinoma |
| Sample 24 | Decreased | Breast adenocarcinoma |
| Sample 25 | Decreased | Colon adenocarcinoma |
| Sample 26 | Variable | Metastatic colon adenocarcinoma |
| Sample 27 | Decreased | Ovarian adenocarcinoma |
| Sample 28 | Decreased | Breast adenocarcinoma |
| Sample 29 | No Effect | Invasive, moderately differentiated adenocarcinoma of colon |
| Sample 30 | No Effect | Cystic poorly differentiated endometroid carcinoma of ovary |
| Sample 31 | Decreased | Ovarian Serous papillary carcinoma |
| Sample 32 | Decreased | Ovarian adenocarcinoma |
| Sample 33 | No Effect | Ovarian adenocarcinoma |
| Sample 34 | No Effect | Metastatic, recurrent moderately to poorly differentiated colonic adenocarcinoma |
| Sample 35 | No Growth | Colonic adenocarcinoma, Gr 3–4, moderately to poorly differentiated |
| Sample 36 | Decreased | Colonic adenocarcinoma, Gr 3–4, moderately to poorly differentiated |
| Sample 37 | Decreased | Cervical squamous cell carcinoma |

TABLE 4

IC50 Data

| Sample Number | IC50 (ng/ml) of AII(1–7) | Diagnosis |
|---|---|---|
| Sample 2 | 3.0 | Ovarian papillary serous carcinoma |
| Sample 4 | 1.0 | Endometrial adenocarcinoma |
| Sample 7 | 2.73 | Breast adenocarcinoma |
| Sample 8 | 1.0 | Endometrial adenocarcinoma |
| Sample 9 | | Endometrial adenocarcinoma |
| Sample 10 | No Effect | Breast adenocarcinoma |
| Sample 11 | No Effect | Endometrial adenocarcinoma |
| Sample 18 | No Effect | Endometrial adenocarcinoma |
| Sample 20 | 0.3 | Breast adenocarcinoma |
| Sample 21 | No Effect | Breast adenocarcinoma |
| Sample 22 | 0.1 | Endometrial adenocarcinoma |
| Sample 23 | 4.0 | Endometrial adenocarcinoma |
| Sample 24 | 4.25 | Breast adenocarcinoma |
| Sample 25 | 4.75 | Colon adenocarcinoma |

TABLE 4-continued

IC50 Data

| Sample Number | IC50 (ng/ml) of AII(1–7) | Diagnosis |
|---|---|---|
| Sample 27 | 3.6 | Ovarian adenocarcinoma |
| Sample 28 | 2.97 | Breast adenocarcinoma |
| Sample 31 | 2.34 | Ovarian Serous papillary carcinoma |
| Sample 32 | 3.4 | Ovarian adenocarcinoma |
| Sample 36 | 2.55 | Colonic adenocarcinoma, Gr 3–4, moderately to poorly differentiated |
| Sample 37 | 2.73 | Cervical squamous cell adenocarcinoma |

A statistical Chi Square analysis of the results reveals that AII(1-7) displays statistically significant tumor-type specificity:

1) Uterine adenocarcinoma: 5 decreased, 2 not affected (71.4% affected), remaining tumors not of this origin 11 decreased, 16 not affected (40.7% affected). p value: 0.306.

2) Breast infiltrating ductal adenocarcinoma: 4 decreased, 2 not affected (66.7% affected), remaining tumors not of this origin 12 decreased, 16 not affected (42% affected). p value: 0.542

3) Uterine adenocarcinoma and breast infiltrating ductal adenocarcinoma: 9 decreased, 4 not affected (69.2% affected), remaining tumors not of this origin 7 decreased, 14 not affected (33.3% affected). p value: 0.092

4) Uterine, ovarian and breast adenocarcinomas: 11 decreased (68.8%), 5 not affected (31.2%), remaining tumors not of this origin 5 decreased (27.8%), 13 not affected (72.2%) p value 0.041

5) All adenocarcinoma: 14 decreased, 8 not affected (63.6% affected), remaining tumors not of this origin 2 decreased, 10 not affected (16.7% affected). p value: 0.024.

We claim:

1. A method for inhibiting tumor cell proliferation, comprising administering to a patient with a tumor an amount effective for inhibiting tumor cell proliferation of at least one active agent comprising a sequence consisting of SEQ ID NO:4, wherein the tumor cell is an adenocarcinoma tumor cell.

2. The method of claim 1 wherein the adenocarcinoma is selected from the group consisting of uterine adenocarcinoma, ovarian adenocarcinoma, and breast adenocarcinoma.

3. The method of claim 1 wherein the adenocarcinoma is a uterine adenocarcinoma.

4. The method of claim 1 wherein the adenocarcinoma is a ovarian adenocarcinoma.

5. The method of claim 1 wherein the adenocarcinoma is a breast adenocarcinoma.

* * * * *